United States Patent [19]
Curtis et al.

[11] Patent Number: 5,833,641
[45] Date of Patent: Nov. 10, 1998

[54] WOUND HEALING MATERIAL

[75] Inventors: Adam Sebastian Genevieve Curtis; Christopher David Wicks Wilkinson, both of Glasgow, United Kingdom

[73] Assignee: The University Court of the University of Glasgow, United Kingdom

[21] Appl. No.: 687,621
[22] PCT Filed: Feb. 20, 1995
[86] PCT No.: PCT/GB95/00350
§ 371 Date: Sep. 19, 1997
§ 102(e) Date: Sep. 19, 1997
[87] PCT Pub. No.: WO95/22305
PCT Pub. Date: Aug. 24, 1995

[30] Foreign Application Priority Data

Feb. 18, 1994 [GB] United Kingdom .................... 9403135

[51] Int. Cl.⁶ ..................................................... A61F 13/00
[52] U.S. Cl. ................................................. 602/43; 602/45
[58] Field of Search ........................ 602/41–59; 623/11, 623/13, 66; 128/DIG. 8; 428/408

[56] References Cited

U.S. PATENT DOCUMENTS 3,929,583 12/1975 Sharpe et al. ........................... 195/127
4,231,660 11/1980 Remy et al. ............................. 356/244
5,607,607 3/1997 Naiman et al. ....................... 219/21.68

FOREIGN PATENT DOCUMENTS 0 145 406 6/1985 European Pat. Off. .
0 562 862 9/1993 European Pat. Off. .
WO92/10218 6/1992 WIPO .

OTHER PUBLICATIONS

P. Clark et al; Topograhical control of cell behaviour; II. multiple grooved substrate, *Development* vol. 108 (4) 1990.
B. Wojciak & J.F. Crossan; The accumulation of inflammatory cells in synovial sheath and epitenon during adhesion formation in healing rat flexor tendons; *Clin Exp Immunol* 93 pp. 108–114 (1993).
P. Clark et al; Cell guidance by ultrafine topography in vitro; *Journal of Cell Science* 99 Part 1 (May 1991).

*Primary Examiner*—Linda C. Dvorak
*Assistant Examiner*—Kim M. Lee
*Attorney, Agent, or Firm*—Bell Seltzer Intellectual Property Law Group of Alston & Bird LLP

[57] ABSTRACT

A device for use in promoting wound healing is made of a substrate formed of a biologically acceptable material and has there on means capable of orienting cell growth so as to allow guided tissue repair. The means for orienting cell growth may include grooves embossed or stamped on a surface of the substrate.

15 Claims, 1 Drawing Sheet

WOUND HEALING MATERIAL

TECHNICAL FIELD

The present invention relates to a device for use in promoting wound healing (whether the wound be the result of an accident, a surgical wound or a wound caused by disease) which allows guided tissue repair so as to encourage the regeneration of tissue of normal function and morphology.

BACKGROUND

The body's capacity to repair itself after accidental wounding or after surgery is often defective because the tissues rebuild with an incorrectly oriented or even with an unoriented structure, or because cells of one type push cells of other types away from their correct positions within the tissue. For example, fibroblasts often form fibrous tissue during wound healing that blocks nerve cell regeneration, or prevents the correct connection of nerves to prosthetic devices. In a similar way, when gums heal after tooth replacement, competition occurs between epithelia and fibroblasts. Problems may also arise with the healing of tendons that have been cut or damaged. Thus, synovial cells become unoriented and stick to epithenon cells, with the result that tendons after healing may adhere to the wall of the synovial canal within which they lie. Furthermore, there is difficulty in rejoining the ends of the tendons themselves, since the tendon is under tension, with the result that a gap may exist between the ends of the cut or torn tendon. In order to achieve a satisfactory repair, this gap has to be bridged by correctly aligned epithenon cells. Even dermal wounds often repair with an incorrect structure, which may result in pain or disfigurement. In the same way, inappropriate cell formations may occur during the healing of abdominal or cardiovascular surgical wounds.

A further problem in the healing of wounds, is the possible introduction of inappropriate cells, such as inflammatory cells into regions of the wound. For example, the accumulation of inflammatory cells in synovial sheath and epitenon in the healing of rat flexor tendons is described by B. Wojciak and J. F. Crossan, Clin. Exp. Immunol. 1993; 93: 108–114.

SUMMARY OF THE INVENTION

A first aspect of the present invention is a device for use in wound healing. The device includes a substrate formed of a biologically-acceptable material which has a series of grooves and ridges formed in a surface of the substrate.

A further aspect of the present invention is a method of healing a wound by applying the above device in or adjacent the wound.

DETAILED DESCRIPTION

Figure 1:
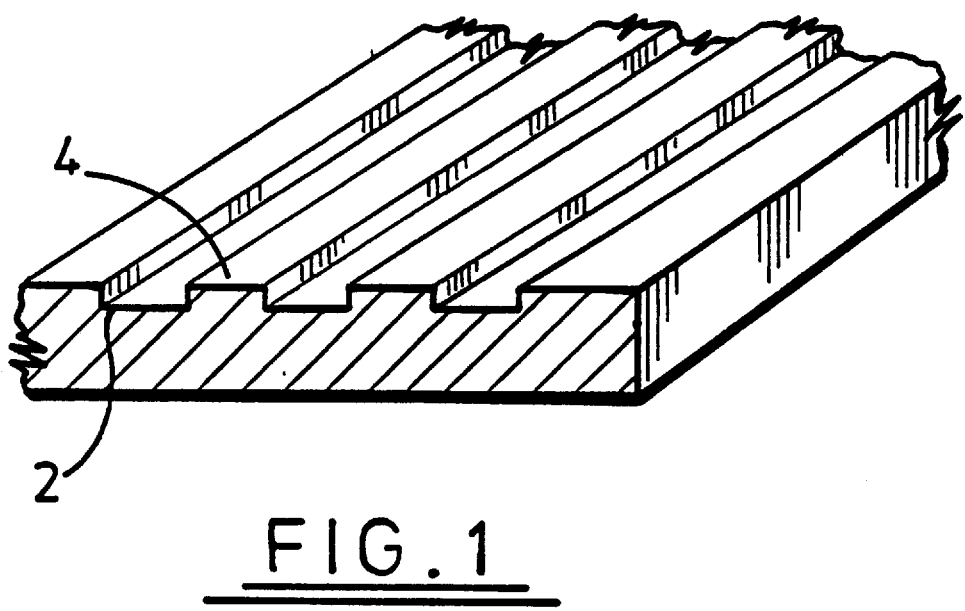
FIG. 1 shows a fragment of a wound healing device of the present invention.

Our European Patent Application EP84308230.6 discloses the location of biological cells in a predetermined spatial disposition on a solid nonbiological substrate, by providing the substrate with a plurality of surface discontinuities defining cell adhesion enhanced and/or cell-adhesion orienting zones, for example grooves or ridges. However, it does not address the issue of wound healing. More recently, the microtopographical control of cell behavior by the use of a grooved substrate has been described by Clark et al,; Development 108; 635–644 (1990).

The use of laser holography and microelectronic techniques to make ultrafine gratings and the behavior of these gratings in aligning cells is described by Clark et al Journal of Cell Science 99; 73–77 (1991).

Whilst these publications describe the orientation of cells in vitro, they do not provide a solution for the production of orderly cell formations during healing of wounds in vivo. It is an object of the present invention to address this problem.

Generally speaking, the present invention is based on the use of means for guiding tissue regeneration during wound healing, thereby encouraging the regeneration of tissue of normal function and morphology.

The present invention provides use of a device in wound healing, the device comprising a substrate formed of a biologically-acceptable material, the substrate having thereon means capable of orienting cell growth.

In another aspect, the invention provides the device itself of use in wound healing.

In a further aspect the invention provides a method of healing wounds in a patient by providing the device in the wound or adjacent the wound site. In this way the orderly growth of cells during the wound healing process is promoted, such that the cellular ordering of the healed wound more closely matches the original cell structuring and function.

The device may be a biodegradable device comprising a biodegradable substrate which becomes resorbed in vivo and effectively disappears from the wound site.

However, in other instances the device may be non-resorbable such as in the case of permanent implants where wound healing is required. Implants including metallic, plastics and ceramic implants are used in connection with joint repair, for example, hip joint prostheses. Such implants may be provided with the cell growth orienting means integrally formed or provided on the surface of the implant itself; or the cell growth orienting means may be on a separate substrate sheet provided on the surface of the implant (such as by wrapping around the implant or adhering thereto). The substrate sheet may be resorbable or non-resorbable.

The term "wound" is to be understood in a broad sense as covering wounds made as a result of an accident, as a result of surgery or dentistry or in relation to wounds caused by disease. Surgical wounds include those made for cosmetic purposes and also for the repair of genetic malformations, such as cleft palate or gargoylism. Wounds may also be produced by various disease states or as a result of infectious organisms, such as for example, ulcers or resulting from septicaemia. A wound will generally comprise a discontinuity in an existing tissue, and healing requires the growth of cells from the edges of the tissue such as to fill the discontinuity. Nothing in the prior art indicates that growth of cells from existing tissue to heal a wound could be promoted by use of the present device.

Thus, it is surprisingly found that the use of a material having cell growth orienting means that may orient cell growth, shape and extension, can be effective in assisting orderly wound healing. It may also prevent cell penetration into inappropriate regions, and prevent the formation of adhesions. The presence of the cell growth orienting means at least during the initial stages of wound healing, may be sufficient to initiate cell growth patterns of adhesive cells which assist orderly cell arrangements; whether or not (in the case of a biodegradable substrate) that substrate is present throughout the entire process of wound healing. In that case, it is generally advantageous that the substrate biodegrades and disappears from within or around the wound site prior to the completion of the healing process, so that the substrate itself does not occupy space which should otherwise be filled with cells, and thus interfere with the wound healing. It has been found desirable that a biodegradable substrate should degrade completely within 2 to 14 days, though this may depend on the severity of the wound and the speed of healing in the particular wound type. It may also depend on the physiology of the particular patient.

The mechanism of biodegradation should rely on substances naturally present in the body at or near a wound site. Usually, biodegradation is brought about by enzymes, which may be free or attached to the surfaces of cells, or by the release of oxidative species via the cells. Materials which are biodegraded by other mechanisms, for example by bacterial action, involving species not normally present in the body are unsuitable.

A wide variety of biodegradable biologically-acceptable materials are known and the skilled man will choose a suitable material, which is able to carry the necessary cell orienting means and have a suitable biodegradation time in vivo. Suitable polymer materials include polylactic acid homopolymers, polyglycollic acid homopolymers, lactic acid-glycollic acid copolymers, polydioxanones, polyoxalates, polydioxanone-glycollic acid copolymers, polylactones (such as polymers of caprolactone and valerolactone), polyhydroxybutyrates, polyhydroxyvalerates, polyorthoesters, polyanhydrides, polypeptides, polyvinylalcohols, polyphosphazenes, and natural polymers (e.g. collagen and polysaccharides). In the case of homopolymeric materials, corresponding copolymers with other such materials may also be used. A detailed discussion of biodegradable polymers is given in S. J. Holland and B. J. Tighe "Biodegradable Polymers", Advances in Pharmaceutical Sciences, 1992, p101–164.

In particular, materials commonly used to produce dissolvable sutures may be suitable. Reconstituted collagen may be employed as the substrate, though its uneven consistency may inhibit the application of suitable microtopography.

Non-biodegradable-medical grade polymers include polyamides, polyethylenes, polypropylenes, polycarbonates, and polyesters.

For sheet-like substrates, the thickness may be up to 250 microns, but is preferably in the range 50–100 microns. The thickness is a factor which determines the flexibility of the device. The time for biodegradation to occur will also depend on the thickness of the substrate.

In a particular embodiment, the device has a flexible nature, which allows it to be inserted into a wound. Three-dimensional tissue repair may be achieved by imparting a three-dimensional configuration to the substrate. In the case of a substrate in sheet-form, it can be folded, rolled, formed into a spiral or stacked structure, or formed into any other shape appropriate to a specific anatomical site or surgical procedure. In particular, the substrate may be in the form of a sheet which has been folded. The substrate may be folded once or a number of times into a concertina-like configuration. Thus, a flexible sheet conformation is particularly useful for insertion into a wound. Flexibility in the substrate also allows it to be wrapped around a structure such as a ligament, tendon, muscle, blood vessel or other elongate structure which requires repair.

The device may also be provided in the form of a tube, optionally a longitudinally split tube, for fitting into or around a wound site, particularly where a substantial gap in the wound exists which requires to be filled with cells during the wound healing process. For instance, a tube may be positioned within the wound to promote cell growth at the centre of the wound; and a tubular substrate may be wrapped around the outside of the wound, in order to promote correct cell growth in the outer regions of the wound. Thus, in the repair of a tendon, it may be advantageous to provide a central tube within the wound between the separated ends of the tendon, together with a tubular sheet of the substrate wrapped around the tendon and tied off around each end with a conventional suture.

A particular use of biodegradable (i.e. resorbable) materials is to form a spacer(s) to hold the device into a configuration which is suitable for packaging, surgical manipulation and implantation; prior to biodegradation thereof in vivo. In one such case, part of the wound healing device may be biodegradable whilst the remainder is formed of a non-degradable material.

The cell growth orienting means may direct the orientation and control the speed of cell movement, and can be in the form of a suitable microtopography and/or suitable microchemistry to influence regrowth. Suitable microtopography to provide orientation of cell growth is already known, as described previously. It may be effective to control cell orientation, cell shape, speed of cell movement, and plane of cell division. For application to the healing of wounds, the microtopography is preferably in the form of a series of peaks and troughs e.g. parallel grooves (and/or ridges). Sharp edged substantially rectangular-section grooves are particularly useful. Preferably, the grooves have a width of 1–10 microns. The width and depth of the grooves is to some extent determined by the nature of the cells which are to be grown. Preferably, the depth of the grooves is from 0.3 to 5 times the average width of the cell when the cell is positioned on a flat surface. Practically speaking, this means that the depth of the groove is generally in the region of 1–10 microns also. Preferably, the ratio of the width of the groove to its depth (i.e. the aspect ratio) is in the region 0.5 to 2, preferably substantially 1:1. Generally, the spacing between the groove edges will be of the same order as the width of the grooves themselves, that is to say 1–10 microns. The groove spacing from centre to centre is generally 2–20 microns. One particular preferred embodiment that has been used for epitenal cells and muscular cells has a groove width 5 microns, groove depth 3 microns and groove spacing (centre to centre) of 10 microns. (i.e. 5 microns between groove edges). Groove size may be chosen to preferentially exclude one cell type (e.g. inflammatory cells) from a specified region and to favour another cell type. Macrophages may be guided by grooves which are of the order of nanometers deep and may be preferentially withdrawn from a site (e.g. a prosthesis) by appropriate choice of groove size.

Another microtopographical structure which may provide the desired degree of cell growth orientation is in the form of a series of rounded protrusions or bumps arranged in a regular array. Preferably the array is a square array (i.e. the protrusions lie on a regular square grid). The cells then tend to grow along the valleys defined between adjacent rows of protrusions.

However, other cell growth orienting arrangements may be used depending on the desired healing growth patterns.

These may include circular or serpentine patterns. Spiral patterns may be used for specialized purposes, since cells growing on a spiral tend to migrate to the region of lowest curvature. This allows an area free of cells or reduced in cell number to be provided in the centre of the spiral.

The microtopographical pattern may be applied in a manner already disclosed in the prior art, and is preferably achieved by embossing directly onto the substrate, for example by passing the substrate between the nip created between an embossing roller and a smooth roller. However, the pattern may be applied to both faces of the substrate by the use of a pair of embossing rollers, if desired. The pattern applied to the two faces may be the same or different.

Embossing of the substrate may be carried out using dies or rollers which have been manufactured using photolithography or electron beam lithography, followed by etching and electro-plating.

It is also possible to orient the cell growth by means of microchemistry, that is to say by chemically providing lines of preferred cell growth on the substrate. Suitable materials for promoting cell adhesion and thus orientation are disclosed in patent specification EP84308230.6. However, the preferred method according to the present invention is to provide strips of cell-adhesive proteins or protenacious material, optionally with layers of specifically non-cell adhesive stripes between.

The device may be surface treated in order to achieve bio-burden control, or modification of the surface chemistry thereof; for example by the use of oxygen plasma techniques.

The device of the present invention is necessarily formed of biologically acceptable material, and can, Of course, be sterilized by known methods, e.g. ethylene oxide, gamma irradiation, or oxygen plasma etching.

Embodiments of the present invention will now be described by way of example only.

EXAMPLE 1
(embossing biodegradable plastic)
(a) Preparation of stamping master formed of polyimide deposited on a plating base.

Onto a glass plate, a 0.1 um (micron) coating of nichrome was deposited by electron beam evaporation in vacuum to form a plating base. Then a 7 um coating of polyimide was put onto the nichrome by spin-coating, and the polyimide fully cured (by a series of bakes, finishing at 300° C.) Alternatively photoresist may be used in place of the polyimide. Onto the cured polyimide, a 0.1 um coating of aluminium was deposited by thermal evaporation, and onto this a 0.5 um layer of positive photoresist was deposited. The photoresist was exposed using UV light to a pattern of 10 um lines, 10 um spaces covering a 10 by 10 mm area by contact printing. The latent image in the resist was developed in resist developer and the resulting relief pattern in resist was used as an etch resistant mask during etching of the aluminium in a wet etch bath (consisting of orthophosphoric acid, nitric acid and water). This aluminium pattern was used as a oxygen-resistant mask in subsequent reactive ion etching of the polyimide in oxygen. In this step, oxygen at a flow rate of 20 sscm, and 20 mT pressure was ionised in a 100 W rf 13.6 MHz discharge. The plasma etches vertically into the polyimide, and the etching stops on the underlying nichrome layer. After stripping of the aluminium mask in aluminium etch, the structure is ready for electroplating.
(b) Making of stamp The structure was placed in a nickel plating bath, the plating base constituting one electrode and a nickel sheet the other electrode. The plating bath was Lectonic obtained from Ethone-omi. The plating bath was made up of nickel sulphate plating solution, an activator, a wetting agent and an adhesion agent following the manufacturer's instructions. Nickel was deposited to a thickness of 50 to 70 um, at a current density of 20 mA/cm$^2$. The nickel shim (stamp) was removed from the glass plate with the aid of a scapel.
(c) Embossing of plastics sheets A biodegradable poly-p-dioxanone plastics from Ethicon Inc., known as Ethicon PDS (trademark), was melted at 110° C. and cast into a glass petri dish. The film was removed from the glass by cutting and peeling, and placed in a press with the stamp on top of it. The press was heated to 100° C. and a force of 5 kN applied. The plastic film was embossed to a depth of 3–4 um and was easily removed from the stamp.

FIG. 1 shows a fragment of the embossed sheet to an enlarged scale, comprising grooves 2 of width 10 um separated by lands 4 of width 10 um.

EXAMPLE 2
(Cell preparation and growth)
(i) Baby Hamster Kidney (BHK) cells were cultured until confluent, then trypsinized, centrifuged and plated onto the embossed structured surfaces, and observed as follows.

The BHK cells (BHK21 C13) cells were cultured in BHK21 culture medium (a modified minimum essential medium supplemented with 0.22% bicarbonate, 10% calf serum, 10% tryptose broth, 2.85 mM glutamine and antibiotics) in 75 cm$^3$ polystyrene culture flasks. When the cells became confluent they were trypsinised with trypsin-versene solution at a trypsin activity of 250 BAEE unit/ml in 0.5 mM EDTA in Hanks saline (free of calcium and magnesium ions) for 5 min at 37° C.

Then the cells were spun at 1400 rpm and resuspended in 5 ml culture medium, kept at room temperature for 10 mins and then spun again. The pellet was resuspended in BHK 21 medium and kept in sterile conditions until used.

Cells were plated onto 33 mm diameter Petri dishes containing the embossed biodegradable plastics sheets or glass coverslips (controls) at a density of $2.10^5$ cells/ml and incubated overnight at 37° C. The cells were examined in an optical microscope. The degree of alignment of the cells to the direction of the grooves was very marked, alignment being essentially complete. The morphology of cells was notably different from cells on plain surfaces; the cells being longer and thinner.
(ii) In another experiment human endothelial cells (GHTEN line) which had been maintained in Hans F10 supplemented with 3% Foztal calf serum and supplements were plated onto the embossed plastics sheets. These endothelial cells are present in the walls of capillary blood vessels. These human endothelial cells showed good alignment along the direction of the grooves in the embossed plastics sheet, and moved more rapidly along the grooves than the other cells.

Minimum essential medium (MEM), Hanks saline and Hans F10 are well known media whose composition is defined in standard text books on cell culture methods (e.g. Freshney R. Ian. "Culture of Animal Cells: A Manual of Basic Technique" (1987) published by Alan R. Liss, Inc. (New York), Second Edition).

EXAMPLE 3
(Rat Tendon)

We used fused silica substrata with multiple grooves in tendon organ culture. The dynamics of tendon healing was compared on plain and patterned substrata. The sensitivity of epitenon cells to topographical features was also studied.

(i) Substratum patterning

Fused silica samples (Multi-lab) were cut into 25 mm$^2$ by 1 mm thick samples. The silica was cleaned by soaking in a solution of 3:1 sulphuric acid:hydrogen peroxide for 5–10 min at 60° C. followed by rinse in R.O. water, then blow dried with filtered air. The silica was coated with photoresist by spinning at 400° rpm for 30 s followed by a soft bake at 90° C. for 30 min. This gave a resist thickness of 1.8 μm. The resist was then patterned by exposing to u.v. light, through a chrome mask patterned with the required grating pattern, using a mask aligner (HTG) for 10 s. The exposed resist was developed off by immersing the sample in a solution of 1:1 Shipley developer R.O. water for 65–75 s followed by a rinse in R.O. water, then blown dry.

The samples were dry etched in a RIE Unit (Plasma Technology). After etching the residual resist was removed, and all samples blanket etched for 1 min.

(ii) Rat Tendon Organ Culture

Flexor tendons were isolated from the middle digit of the hind paw of male Sprague Dawley rats. Twelve 8-weeks-old rats were anaesthesized using halothane. Synovial sheath was removed and the tendons were divided and placed on to plain and patterned fused silica substrata (grooves 5 μm deep, 10 μm wide) so that the gap between two tendon ends was 0.5 mm wide. Tendons were placed in parallel to the direction of the grooves and pressed with a clean coverslip. Tendons were incubated in BHK culture medium (20 mM HEPES buffered Glasgow modified MEM (Gibco BRL, Life Technologies, Paisley, UK)) supplemented with 0.5% bicarbonate, 10% foetal calf serum (Gibco), 10% tryptose broth (Gibco), 285 mM glutamine, antibiotics, for 3 weeks. The medium was changed every 48 h. After 3 and 5 weeks tendons were used for frozen sections and histological staining. Some of the healing tendons were studied under a light scanning confocal microscope.

On plain substrata, healing did not occur over a period of 8 weeks. During this time proliferation of epitonen cells occurred on the tendon surface close to the divided tendon ends. The epitonen layer thickened to become 3–6 cells thick. These proliferating cells then migrated round the surface of the divided end so that their long axis lay at right angles to the long axis of the tendon. There was no evidence of significant migration across the gap to restore continuity between the tendon segments. Similarly, extracellular matrix was laid down in the same orientation so that the tendon ends became rounded off.

In contrast, when tendon segments were placed together in the same orientation as the grooves on the microfabricated substrata according to the invention, reconstitution of the tendon occurred within 8 weeks in most experiments. The tendon ends became bullet-shaped, rather than being rounded off and thus approached one another. A considerable degree of epitonen proliferation occurred close to the site of the division, but instead of migrating over the surface of the end of the tendon, they formed a highly cellular advancing front which started to fuse with similar tissue from the opposite tendon at about 3 weeks. Over the next 3 weeks practically all of these advancing cells disappeared, leaving a loosely bound mass of extracellular matrix aligned in the long axis of the tendon so that continuity was restored. The histology of the restored tendon was nearly normal.

(iii) Rat Epitenon Cell Culture

Rat epitenon fibroblasts were isolated from rat flexor tendons of male Sprague Dawley rats. Briefly, in step 1, the synovial sheath was removed by incubation of tendons in 0.5% collagenase (Clostridiopeptidase A; EC 3.4.24; Sigma Chemical Co. Poole, UK) for 10 min at 37° C.

In step 2 tendons were incubated in trypsin/EDTA solution (trypsin, 300 BAEE (N α-benzoyl-L-arginine ethyl ester) U/ml; EDTA, 0.001 m EDTA) for 1.5, at 37° C. then the released cells were suspended in BHK21 medium and centrifuged at 200 g for 6 min. Cells were then resuspended in the culture medium (BHK21) and plated into 25 cm$^2$ Falcon culture flasks at cell density $2 \times 10^5$ cells/ml. For experiments they were used between 15 and 25 passages.

For experiments epitenon cells were plated on to plain and patterned fused silica substrates at cell density $2 \times 10^5$ cells/ml. After 24 h cells were washed in serum-free Hank's balanced salt solution and fixed in 4% formaldehyde in phosphate-buffered saline (PBS) for 5 min. Then the cells were washed again in PBS, stained in Kenacid blue (Sigma, UK) (0.1% in water/methanol/acetic acid, 50:50:7) for 10 min, and analysed using an image analysis system.

Cell spread area, elongation and orientation (alignment to the groove direction) was measured in epitenon cells cultured on plain and patterned substratum with varying groove depth and width. This study has been done to establish the sensitivity of epitenon cells to topographical features and find groove parameters that create the best conditions for the guidance of tendon cells. The guidance of epitenon cells was compared to the guidance of BHK cells. Although the two cell lines were obtained from different species, they represent cell of the same type (fibroblasts) and size (spreading area $2800 \pm 1200$ μm$^2$).

Epitenon cells were well guided by multiple grooved substrata. They responded to topographical features by a substantial elongation. Their elongation did not depend on groove width but showed some dependence on groove depth (one way analysis of variance, $p<0.01$). The best elongation was achieved for 2 and 5 μm deep grooves. Elongation of BHK cells depended both on groove depth and width. Epitenon cells were significantly better elongated than BHK fibroblasts on shallow grooves 0.5 and 1 μm deep ($p<0.05$).

Epitenon cells were very well oriented on all kinds of grooved substrata, although a decrease in cell orientation was seen for cells grown on shallow grooves, 0.5 μm deep. This is documented by low variance in the tested samples. BHK cells were well oriented by grooves 2 and 5 μm deep but less oriented by grooves 1 and 0.5 μm deep. Vaiance for BHK cells was higher than for epitenon cells on all kinds of patterned substrata which shows that epitenon cells are more sensitive to topographical features than BHK fibroblasts.

What is claimed is:

1. A device for use in wound healing, which comprises a substrate formed of a biologically-acceptable biodegradable material adapted to become resorbed in use, the substrate having thereon means capable of orienting cell growth comprising a series of grooves and ridges, the grooves and ridges being formed in a surface of the substrate.

2. A device according to claim 1 wherein the biodegradable substrate is a poly-p-dioxanone polymer.

3. A device according to claim 1 wherein the substrate is flexible, so as to allow it to be inserted into the wound.

4. A device according to claim 1 wherein the substrate is in the form of a sheet.

5. A device according to claim 4 wherein the sheet has a thickness in the range 50–100 microns.

6. A device according to claim 4 wherein the sheet is folded, rolled or otherwise formed into a three-dimensional configuration adapted for insertion into the wound.

7. A device according to claim 1 wherein the depth of the grooves is from 0.3 to 5 times the average width of the type of cell which is to be grown thereon, the average width of the cell being the width thereof when the cell is positioned on a flat surface.

8. A device according to claim 1 wherein the depth of each groove is in the region 1–10 microns.

9. A device according to claim 1 wherein the width of each groove is in the region 1–10 microns.

10. A device according to claim 1 wherein the ratio of the width of each groove to its depth is in the region 0.5 to 2.

11. A device according to claim 1 wherein the spacing of the grooves from centre-to-centre is in the region 2 to 20 microns.

12. A device according to claim 1 wherein the means capable of orienting cell growth have been applied to the substrate by embossing.

13. A method of healing a wound in a patient by providing a device according to claim 1 in the vicinity of the wound, said device promoting oriented cell growth during wound healing such that the cellular ordering of the healed wound matches the original cell structuring and function.

14. A device according to claim 1, wherein the substrate is biodegradable and is adapted to become resorbed in use.

15. A method of healing a wound according to claim 13, wherein said oriented cell growth occurs in cells selected from the group consisting of tendon cells, fibroblasts and endothelial cells.

* * * * *

UNITED STATES PATENT AND TRADEMARK OFFICE
CERTIFICATE OF CORRECTION

PATENT NO.   : 5,833,641

DATED        : November 10, 1998

INVENTOR(S)  : Curtis et al.

It is certified that error appears in the above-identified patent and that said Letters Patent is hereby corrected as shown below:

Title Page, Item [86]:

Sections 371 and 102(e) dates, "Sep. 19, 1997" should read --Sep. 19, 1996--.

Signed and Sealed this

Twentieth Day of April, 1999

Attest:

Q. TODD DICKINSON

Attesting Officer

Acting Commissioner of Patents and Trademarks